US006730775B1

(12) United States Patent
Rodgers et al.

(10) Patent No.: US 6,730,775 B1
(45) Date of Patent: May 4, 2004

(54) METHODS FOR LIMITING SCAR AND ADHESION FORMATION

(75) Inventors: Kathleen E. Rodgers, Long Beach, CA (US); Gere diZerega, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/532,221

(22) Filed: Mar. 22, 2000

Related U.S. Application Data

(60) Provisional application No. 60/125,707, filed on Mar. 23, 1999, and provisional application No. 60/139,541, filed on Jun. 16, 1999.

(51) Int. Cl.$^7$ .......................... A61K 38/00; A61K 38/04
(52) U.S. Cl. ....................... 530/316; 530/328; 530/329; 514/16
(58) Field of Search ............................ 514/16; 530/316, 530/328, 329

(56) References Cited

U.S. PATENT DOCUMENTS

| | | | |
|---|---|---|---|
| 4,889,722 A | 12/1989 | Sheffield et al. | |
| 5,015,629 A | 5/1991 | diZerega | |
| 5,478,837 A | 12/1995 | Rodgers et al. | |
| 5,498,613 A | 3/1996 | Rodgers et al. | |
| 5,534,261 A | 7/1996 | Rodgers et al. | |
| 5,614,515 A | 3/1997 | Rodgers et al. | |
| 5,629,292 A | 5/1997 | Rodgers et al. | |
| 5,629,294 A | 5/1997 | diZerega et al. | |
| 5,639,468 A | 6/1997 | Rodgers et al. | |
| 5,693,616 A | 12/1997 | Krstenansky et al. | |
| 5,716,935 A | 2/1998 | Rodgers et al. | |
| 5,835,432 A | 11/1998 | Nakano | |
| 5,891,460 A | 4/1999 | Rodgers et al. | |
| 5,955,430 A | * 9/1999 | Rodgers et al. | ............... 514/16 |
| 5,977,159 A | 11/1999 | Faudriks et al. | |
| 6,165,978 A | 12/2000 | Rodgers et al. | |
| 6,455,501 B1 | 9/2002 | Rodgers et al. | |

FOREIGN PATENT DOCUMENTS

| | | |
|---|---|---|
| WO | WO 95/08337 | 3/1995 |
| WO | WO 95/08565 | 3/1995 |
| WO | WO 96/14858 | 5/1996 |
| WO | WO 96/15795 | 5/1996 |
| WO | WO 96/39164 | 12/1996 |
| WO | WO 96/40090 | 12/1996 |
| WO | WO 98/26795 | 6/1998 |
| WO | WO 98/32457 | 7/1998 |
| WO | WO 98/33813 | 8/1998 |
| WO | WO 99/26644 | 6/1999 |
| WO | WO 99/31125 | 8/1999 |
| WO | WO 99/39743 | 8/1999 |
| WO | WO 99/40103 | 8/1999 |
| WO | WO 99/40106 | 8/1999 |
| WO | WO 99/40107 | 8/1999 |
| WO | WO 99/42122 | 8/1999 |
| WO | WO 99/42123 | 8/1999 |
| WO | WO 99/45945 | 9/1999 |
| WO | WO 99/46285 | 9/1999 |
| WO | WO 99/52540 | 10/1999 |
| WO | WO 99/58140 | 11/1999 |
| WO | WO 00/02905 | 1/2000 |
| WO | WO 00/09144 | 2/2000 |

OTHER PUBLICATIONS

Rodgers et al., Database: Issued_Patents_AA, US–08–465–775–4, 1999.*
Chamberlin et al., (1995) *J. Anat.* vol. 186: pp. 87–96.
Ashcroft et al., (1997) *J. Anat.*, vol. 190, pp. 351–365.
Shah et al., (1999) *Am. J. Pathol.*, vol. 154, pp. 1115–1124.
Shah et al., (1994) *J. Cell Science*, vol., 107, pp. 1137–1157.
Kunapuli et al., (1987) *Circulation Research*, vol. 60, pp. 786–790.
Clouston et al., (1988) *Genomics*, vol. 2, pp. 240–248.
Kageyama et al., (1984) *Biochemistry*, vol. 23, pp. 3603–3609.
Ohkubo et al., (1983) *Proc. Natl. Acad. Sci.*, vol. 80, pp. 2196–2200.
Dzau et al., (1989) *J. Mol. Cell Cardiol.*, vol. 21, pp. S7.
Berk et al., (1989) *Hypertension*, vol. 13, pp. 305–314.
Kawahara et al., (1988) *BBRC* vol. 150, pp. 52–59.
Naftilan et al., (1989) *J. Clin. Invest.*, vol. 83, pp. 1419–1423.
Taubman et al. (1989) *J. Biol. Chem.*, vol. 264, pp. 526–530.
Nakahara et al., (1992) *BBRC*, vol. 184, pp. 811–818.
Stouffer et al., (1992) *Circ. Res.*, vol. 70, pp. 820–828.
Wolf et al., (1992) *Am. J. Pathol.*, vol. 140, pp. 95–107.
Bell et al., (1990) *Am. J. Pathol.*, vol. 137, pp. 7–12.
Fernandez et al., (1985) *J. Lab. Clin. Med.*, vol. 105 pp. 141–145.
LeNoble, et al., (1991) *Eur. J. Pharmacol.*, vol. 195, pp. 305–306.
Shanugam et al., (1995) *Am. J. Physiol.*, vol. 268, pp. F922–F930.
Helin et al., (1997) *Annals of Medicine*, vol. 29, pp. 23–29.
Bedecs et al., (1997) *Biochem J.*, vol. 325, pp. 499–454.
Steckelings et al., (1996) *Biochem. Biophys. Res. Commun.*, vol. 229, pp. 329–333.
Janiak et al., (1992) *Hypertension*, vol. 20, pp. 737–745.
Prescott et al., (1991) *Am J. Pathol.*, vol. 139, pp. 1291–1296.
Kauffman et al., (1991), *Life Sci.*, vol. 49, pp 223–228.

(List continued on next page.)

*Primary Examiner*—Christopher S. F. Low
*Assistant Examiner*—Rita Mitra
(74) *Attorney, Agent, or Firm*—McDonnell Boehnen Hulbert & Beghoff

(57) ABSTRACT

The present invention provides methods, kits, and pharmaceutical compositions for limiting scar or adhesion formation by administration of angiotensinogen, AI, AI analogues, and/or AI fragments and analogues thereof, AII analogues, AII fragments or analogues thereof, ACE inhibitors, AII $AT_2$ type 2 receptor agonists, either alone or in combination with other compounds.

19 Claims, 11 Drawing Sheets

OTHER PUBLICATIONS

Viswanathan, et al.,(1992), *Peptides*, vol. 13, pp. 783–786.
Kimura, et al., (1992), *BBRC*, vol. 187, pp. 1083–1090.
Pfeilschifter, et al., (1992), *Eur. J. Pharmacol.*, vol. 225, pp. 57–62.
Jaiswal, et al., (1992), *Hypertension*, vol. 19, (Supp. II): II–49–II–55.
Edwards et al., (1993), *J. Pharmacol. Exper. Ther.*, vol. 266, pp. 506–510.
Jaiswal, et al., (1991), *J. Pharmacol. Exper. Ther.*, vol. 265, pp. 664–673.
Jaiswal, et al., (1991), *Hypertension*, vol. 17, pp. 1115–1120.
Portisi, et al., (1994), *Br. J. Pharmacol.* vol. 111, pp. 652–654.
Ferrario et al, (1998), *J. Am. Soc. Nephrol.*, vol. 9, pp. 1716–1722.
Iyer et al., (1998), *Hypertension*, vol. 31, pp. 699–705.
Freeman et al., (1996), *Hypertension*, vol. 28, pp. 104–108.
Ambuhl et al., (1994), *Brain Res. Bull.*, vol. 35, pp. 289–291.
Ferrario et al, (1997), *Hypertension*, vol. 30, pp. 535–541.
Catalioto et al., (1994) *Eur. J. Pharmacol*, vol. 256, pp. 93–97.
Bryson et al., (1992), *Eur. J. Pharmacol.*, vol. 225, pp. 119–127.
Regoli et al., (1974), *Pharmacological Reviews*, vol. 26, pp. 69.
Rodgers et al., (1998), *Fertility and Sterility*, vol. 70, pp. 1131–1138.
Rodgers et al., (1996), *J. Invest. Surg.*, vol. 9, pp. 385–391.
Rodgers et al., (1997), *J. Invest. Surg.*, vol. 10, pp. 31–36.
Legrand et al., (1995), *J. Invest. Surg.*, vol. 8, pp. 187–194.
Nishimura, et al., (1984), *Am. J. Med.*, vol. 77, pp. 102–106.

* cited by examiner

SEQUENCE LISTING

```
<160> NUMBER OF SEQ ID NOS: 50

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:AII

<400> SEQUENCE: 1

Asp Arg Val Tyr Ile His Pro Phe
  1               5

<210> SEQ ID NO 2
<211> LENGTH: 7
<212> TYPE: PRT
```

```
<213> ORGANISM: Artificial Sequence
<220> FEATURE:
<223> OTHER INFORMATION: Description of Artificial Sequence:AII (2-8)

<400> SEQUENCE: 2

Arg Val Tyr Ile His Pro Phe
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:AII (3-8)

<400> SEQUENCE: 3

Val Tyr Ile His Pro Phe
  1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:AII (1-7)

<400> SEQUENCE: 4

Asp Arg Val Tyr Ile His Pro
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:AII (2-7)

<400> SEQUENCE: 5

Arg Val Tyr Ile His Pro
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:AII (3-7)

<400> SEQUENCE: 6

Val Tyr Ile His Pro
  1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:AII (5-8)

<400> SEQUENCE: 7

Ile His Pro Phe
  1

<210> SEQ ID NO 8
<211> LENGTH: 6
<212> TYPE: PRT
<213> ORGANISM: Artificial Sequence
```

```
<220> FEATURE:
<223> OTHER INFORMATION: Description of Artificial Sequence:AII (1-6)

<400> SEQUENCE: 8

Asp Arg Val Tyr Ile His
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:AII (1-5)

<400> SEQUENCE: 9

Asp Arg Val Tyr Ile
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:AII (1-4)

<400> SEQUENCE: 10

Asp Arg Val Tyr
 1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:AII (1-3)

<400> SEQUENCE: 11

Asp Arg Val
 1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (2)
<223> OTHER INFORMATION: Nle

<400> SEQUENCE: 12

Arg Xaa Tyr Ile His Pro Phe
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (4)
<223> OTHER INFORMATION: Nle

<400> SEQUENCE: 13

Arg Val Tyr Xaa His Pro Phe
```

```
  1               5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence:AII (6-8)

<400> SEQUENCE: 14

His Pro Phe
  1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:AII (4-8)

<400> SEQUENCE: 15

Tyr Ile His Pro Phe
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:AII analogue
      class
<220> FEATURE:
<221> NAME/KEY: UNSURE
<222> LOCATION: (1)
<223> OTHER INFORMATION: Xaa at position 1 can be Arg, Lys, Ala, Orn,
      Ser, MeGly, D-Arg, or D-Lys
<220> FEATURE:
<221> NAME/KEY: UNSURE
<222> LOCATION: (2)
<223> OTHER INFORMATION: Xaa at position 2 can be Val, Ala, Leu, Nle,
      Ile, Gly, Pro, Aib, Acp, or Tyr
<220> FEATURE:
<221> NAME/KEY: UNSURE
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
  1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 17

Arg Val Tyr Gly His Pro Phe
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 18
```

Arg Val Tyr Ala His Pro Phe
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:AII analogue
      1

<400> SEQUENCE: 19

Asp Arg Val Tyr Val His Pro Phe
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:AII analogue
      2

<400> SEQUENCE: 20

Asn Arg Val Tyr Val His Pro Phe
1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:AII analogue
      3

<400> SEQUENCE: 21

Ala Pro Gly Asp Arg Ile Tyr Val His Pro Phe
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:AII analogue
      4

<400> SEQUENCE: 22

Glu Arg Val Tyr Ile His Pro Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:AII analogue
      5

<400> SEQUENCE: 23

Asp Lys Val Tyr Ile His Pro Phe
1               5

<210> SEQ ID NO 24
<211> LENGTH: 8
<212> TYPE: PRT
<213> ORGANISM: Artificial Sequence

```
<220> FEATURE:
<223> OTHER INFORMATION: Description of Artificial Sequence:AII analogue
      6

<400> SEQUENCE: 24

Asp Arg Ala Tyr Ile His Pro Phe
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:AII analogue
      7

<400> SEQUENCE: 25

Asp Arg Val Thr Ile His Pro Phe
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:AII analogue
      8

<400> SEQUENCE: 26

Asp Arg Val Tyr Leu His Pro Phe
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:AII analogue
      9

<400> SEQUENCE: 27

Asp Arg Val Tyr Ile Arg Pro Phe
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:AII analogue
      10

<400> SEQUENCE: 28

Asp Arg Val Tyr Ile His Ala Phe
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:AII analogue
      11

<400> SEQUENCE: 29

Asp Arg Val Tyr Ile His Pro Tyr
 1               5
```

```
<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:AII analogue
      12

<400> SEQUENCE: 30

Pro Arg Val Tyr Ile His Pro Phe
  1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:AII analogue
      13

<400> SEQUENCE: 31

Asp Arg Pro Tyr Ile His Pro Phe
  1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:AII analogue
      14
<220> FEATURE:
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
  1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:AII analogue
      15
<220> FEATURE:
<221> NAME/KEY: MOD_RES
<222> LOCATION: (3)
<223> OTHER INFORMATION: Nle

<400> SEQUENCE: 33

Asp Arg Xaa Tyr Ile His Pro Phe
  1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:AII analogue
      16
<220> FEATURE:
<221> NAME/KEY: MOD_RES
<222> LOCATION: (5)
<223> OTHER INFORMATION: Nle

<400> SEQUENCE: 34
```

```
Asp Arg Val Tyr Xaa His Pro Phe
  1               5
```

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:AII analogue
      17
<220> FEATURE:
<221> NAME/KEY: MOD_RES
<222> LOCATION: (4)
<223> OTHER INFORMATION: homo Ser

<400> SEQUENCE: 35

```
Asp Arg Val Ser Tyr Ile His Pro Phe
  1               5
```

<210> SEQ ID NO 36
<211> LENGTH: 8
<212> TYPE: PRT
<213> ORGANISM: Artificial Sequence
<220> FEATURE:
<223> OTHER INFORMATION: Description of Artificial
      Sequence:p-aminophenylalanine 6 AII
<220> FEATURE:
<221> NAME/KEY: MOD_RES
<222> LOCATION: (6)
<223> OTHER INFORMATION: p-aminophenylalanine

<400> SEQUENCE: 36

```
Asp Arg Val Tyr Ile Xaa Pro Phe
  1               5
```

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:angiotensin
      I

<400> SEQUENCE: 37

```
Asp Arg Val Tyr Ile His Pro Phe His Leu
  1               5                  10
```

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:
      1GD:Ala4-AII(1-7)

<400> SEQUENCE: 38

```
Asp Arg Val Ala Ile His Pro
  1               5
```

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: 2GD
      Pro3-AII(1-7)

<400> SEQUENCE: 39

Asp Arg Pro Tyr Ile His Pro

```
<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: 5GD Lys
      3-AII(1-7)

<400> SEQUENCE: 40

Asp Arg Lys Tyr Ile His Pro
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: 9GD
      Norleu-AII(1-7)
<220> FEATURE:
<221> NAME/KEY: MOD_RES
<222> LOCATION: (3)
<223> OTHER INFORMATION: Nle

<400> SEQUENCE: 41

Asp Arg Xaa Tyr Ile His Pro
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence GSD28
      Ile8-AII

<400> SEQUENCE: 42

Asp Arg Val Tyr Ile His Pro Ile
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence:
      Ala3aminoPhe6-AII
<220> FEATURE:
<221> NAME/KEY: MOD_RES
<222> LOCATION: (6)
<223> OTHER INFORMATION: aminophenyalanine

<400> SEQUENCE: 43

Asp Arg Ala Tyr Ile Xaa Pro Phe
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Ala3-AIII

<400> SEQUENCE: 44

Arg Val Ala Ile His Pro Phe
 1               5
```

```
<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence:Gly1-AII

<400> SEQUENCE: 45

Gly Arg Val Tyr Ile His Pro Phe
 1               5

<210> SEQ ID NO 46
<211> LENGTH: 8
<212> TYPE: PRT
<213> ORGANISM: Artificial Sequence
<220> FEATURE:
<221> NAME/KEY: MOD_RES
<222> LOCATION: (4)
<223> OTHER INFORMATION: Nle
<220> FEATURE:
<223> OTHER INFORMATION: Description of Artificial Sequence:
      Norleu4-AIII

<400> SEQUENCE: 46

Arg Val Tyr Xaa Leu His Pro Phe
 1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Acpc3-AII
<220> FEATURE:
<221> NAME/KEY: MOD_RES
<222> LOCATION: (3)
<223> OTHER INFORMATION: 1-aminocyclopentane carboxylic acid

<400> SEQUENCE: 47

Asp Arg Xaa Tyr Ile His Pro Phe
 1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Orn2-AII
<220> FEATURE:
<221> NAME/KEY: MOD_RES
<222> LOCATION: (2)
<223> OTHER INFORMATION: Orn

<400> SEQUENCE: 48

Asp Xaa Val Tyr Ile His Pro Phe
 1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Citron2-AII
<220> FEATURE:
<221> NAME/KEY: MOD_RES
<222> LOCATION: (2)
<223> OTHER INFORMATION: Citron

<400> SEQUENCE: 49
```

```
-continued

Asp Xaa Val Tyr Ile His Pro Phe
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:
      Pro3Ala4-AII(1-7)

<400> SEQUENCE: 50

Asp Arg Pro Ala Ile His Pro
  1               5
```

METHODS FOR LIMITING SCAR AND ADHESION FORMATION

CROSS-REFERENCE

This application claims priority to U.S. Provisional Patent Application Nos. 60/125,707 (filed Mar. 23, 1999) and 60/139,541 (filed Jun. 16, 1999), both references incorporated by reference herein in their entirety.

FIELD OF THE INVENTION

This present invention relates to methods to limit scar and adhesion formation.

BACKGROUND OF THE INVENTION

Wounds in mammalian tissue result in tissue disruption and coagulation of the microvasculature at the wound face. Repair of such tissue represents an orderly, controlled cellular response to injury. The cellular morphology consists of three distinct zones. The central avascular wound space is oxygen deficient, acidotic and hypercarbic, and has high lactate levels. Adjacent to the wound space is a gradient zone of local anemia (ischemia) which is populated by dividing fibroblasts. Behind the leading zone is an area of active collagen and other extracellular matrix protein synthesis characterized by mature fibroblasts and numerous newly-formed capillaries (i.e., neovascularization).

Tissue injuries, such as an injury to the skin due to a laceration, a puncture, or a burn result in a wound that can extend into or through the tissue. If the wound is fairly small and localized, normal healing processes can close the wound and restore normal function to the tissue. (Id.) In some cases, however, an injury results in a deep wound or a wound that affects a large area. Such wounds can require clinical intervention for healing to occur. Wound closure is achieved by the combined action of keratinocyte migration into the wound site and contraction of specialized fibroblasts in the tissue underneath the wound site, which pulls the edges of the wound closer together. Inefficient remodeling of the wound bed leaves a scar, and in severe cases can lead to loss of tissue function at the wound site.

Scars can be defined as a macroscopic alteration in the appearance of the skin resulting from some type of wound, often due to an abnormal organization of dermal connective tissues and their associated cells. (Chamberlin et al., J. Anat. 186:87–96 (1995)) A scar is an imperfect substitute for the original tissue, since it serves as a diffusion barrier to nutrients and oxygen, has a lower breaking strength, and often results in deformation, reduction in function, and impairment of growth of the original tissue. The only advantage offered by a scar is the rapidity by which it allows structural integrity to be established. Thus, the ideal situation for a healing wound would be a rapid closure of the wound and regeneration of the dermal architecture without the formation of a scar and its resultant deleterious effects on growth, function, and appearance. (Chamberlin et al., J. Anat. 186:87–96 (1995))

Fetal wounds, unlike those in the adult, heal without scar formation and with a reduced growth factor profile and inflammatory response. (Chamberlin et al., J. Anat. 186:87–96 (1995)) It has also been demonstrated that, in a well characterized aging mouse colony, the rate of scarring is reduced with age, while healing is delayed in terms of re-epithelialization and basement membrane and matrix deposition. (Ashcroft et al., J. Anat. 190:351–365 (1997)). Thus, the processes of wound healing and scar formation are separable.

Previous studies have demonstrated that a reduction in the levels of transforming growth factor β-1 and β-2 (TGF β-1 and TGF β-2) in healing adult rodent dermal wounds produces no deleterious effects on the speed or strength of wound healing, but provides a reduction in scarring. (Chamberlin et al., J. Anat. 186:87–96 (1995)) Wounds treated with a neutralizing antibody to TGF-β1 have a lower inflammatory response, reduced early extracellular matrix (ECM) deposition, and reduced later cutaneous scarring. (Shah et al., Am. J. Pathol. 154:1115–1124 (1999)) In contrast, increasing the local tissue levels of TGF-β1 increases early ECM deposition, but does not alter scar formation. Thus, factors that promote wound healing do not necessarily limit scar formation.

Scarring is a major cause of many clinical problems. Post-burn contractures, post-operative adhesion and strictures causing intestinal obstructions, mid-facial contractures following cleft palate surgery, and painful neuromas are but a few examples of the problems caused by scarring. Scar tissue interferes with growth, caused deformities, impairs function, and is aesthetically unsightly. (Shah et al., J. Cell Science 107:1137–1157 (1994)).

Similarly, post-operative adhesion formation is a major source of postoperative morbidity and mortality after many surgical procedures, including abdominal, pelvic, thoracic, and other surgical procedures. The pathogenesis of adhesion formation is complex and not entirely understood. The first step is believed to involve excess fibrin deposition to form a scaffold. Organization of the fibrin scaffold by cellular elements, including fibroblasts and mesothelial cells, then follows. A variety of approaches for the prevention of adhesion formation have been actively explored. (See, for example, U.S. Pat. Nos. 5,891,460; 5,639,468; 5,629,294; 5,614,515; 5,534,261; 5,498,613 and 5,478,837; all herein incorporated by reference in their entirety.) However, no single therapeutic approach has proven universally effective in preventing adhesion formation after surgery, or other types of wounds.

Therefore, there is a need for compositions and methods which may be used safely and effectively to limit scar and adhesion formation.

SUMMARY OF THE INVENTION

The present invention provides pharmaceutical compositions, methods, and kits for limiting scar and adhesion formation, comprising administering to a mammal in need thereof an amount effective to limit scar or adhesion formation of angiotensinogen, angiotensin I (AI), AI analogues, AI fragments and analogues thereof, angiotensin II (AII) analogues, AII fragments or analogues thereof, ACE inhibitors, or AII $AT_2$ type 2 receptor agonists, either alone or in combination with other compounds.

DETAILED DESCRIPTION OF THE PREFERRED EMBODIMENTS

Figure 1:
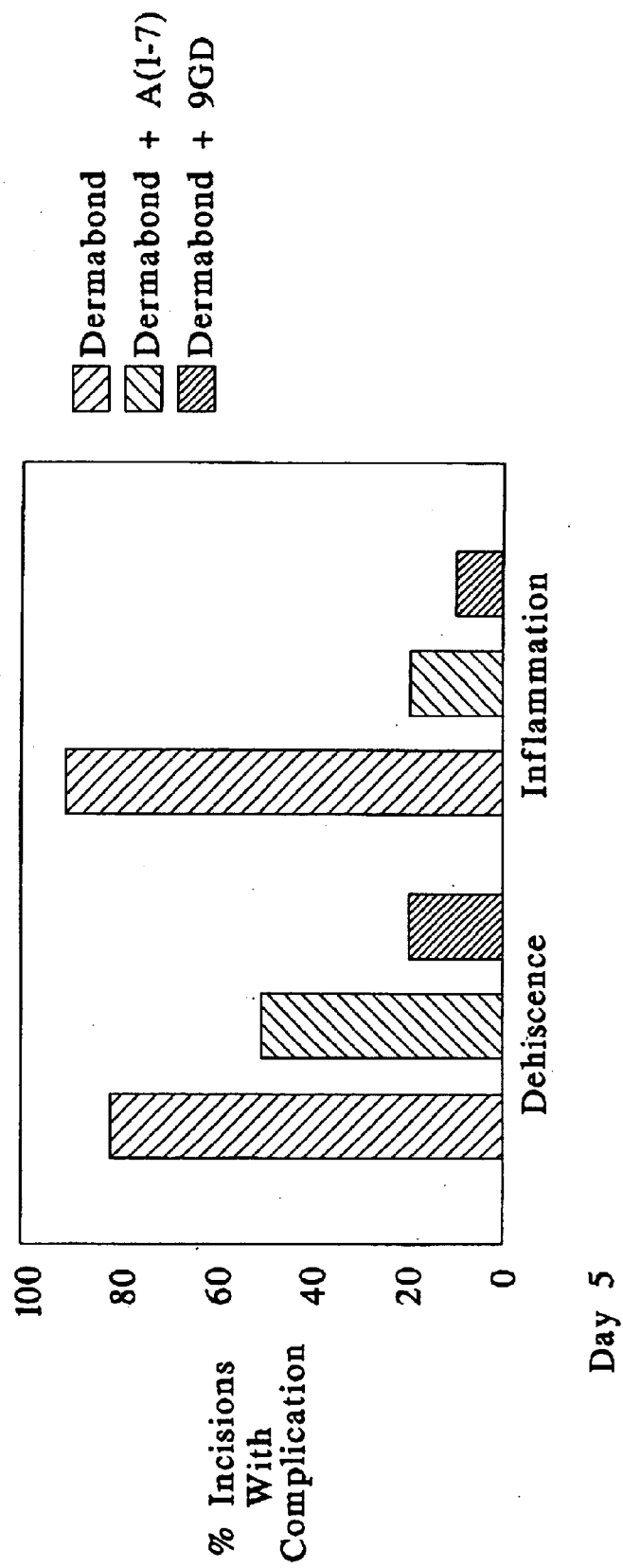
FIG. 1 is a graph showing the effect of AII(1–7) and 9GD on the percent of incisions with dehiscence or inflammation on day 5 in the rat dorsal incision model.
Figure 2:
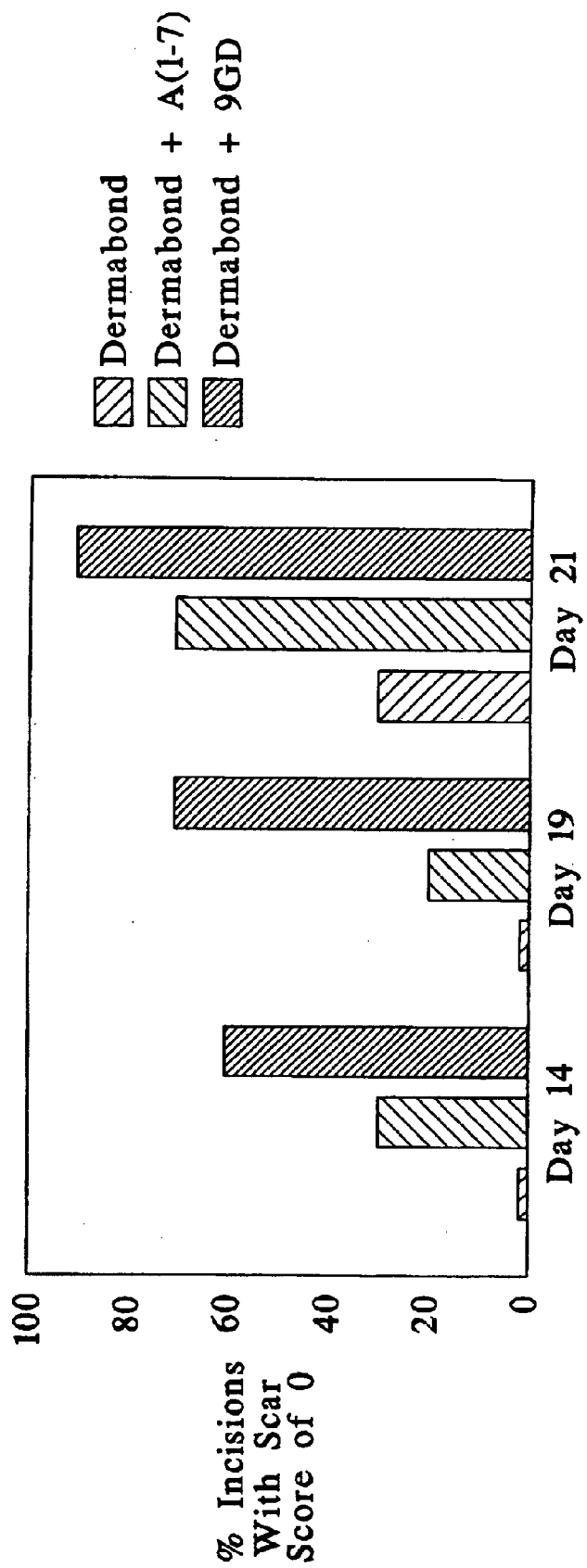
FIG. 2 is a graph showing the effect of AII(1–7) and 9GD on scar formation on days 14, 19, and 21.

All cited patents, patent applications and references are hereby incorporated by reference in their entirety.

As used herein, the term "scar" refers to a macroscopic alteration in the appearance of the skin resulting from some type of wound.

As used herein, the term "adhesion" refers to scar tissue that form between organs and tissue layers.

As used herein, the term "limiting scar formation" refers to decreasing the macroscopic alteration in the appearance of the skin, both prophylactically, by limiting initial scar formation, and therapeutically, by reducing existing scarring.

As used herein, the term "limiting adhesion formation" refers to decreasing the scar tissue that form between organs and tissue layers.

Unless otherwise indicated, the term "active agents" as used herein refers to the group of compounds comprising angiotensinogen, angiotensin I (AI), AI analogues, AI fragments and analogues thereof, angiotensin II (AII) analogues, AII fragments or analogues thereof or AII $AT_2$ type 2 receptor agonists, either alone, combined, or in further combination with other compounds, for limiting scar formation.

Unless otherwise indicated, the term "angiotensin converting enzyme inhibitors" or "ACE inhibitors" includes any compound that inhibits the conversion of the decapeptide angiotensin I to angiotensin II, and include but are not limited to alacepril, alatriopril, altiopril calcium, ancovenin, benazepril, benazepril hydrochloride, benazeprilat, benzazepril, benzoylcaptopril, captopril, captopril-cysteine, captopril-glutathione, ceranapril, ceranopril, ceronapril, cilazapril, cilazaprilat, converstatin, delapril, delapril-diacid, enalapril, enalaprilat, enalkiren, enapril, epicaptopril, foroxymithine, fosfenopril, fosenopril, fosenopril sodium, fosinopril, fosinopril sodium, fosinoprilat, fosinoprilic acid, glycopril, hemorphin-4, idapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. (See for example Jackson, et al., Renin and Angiotensin in Goodman & Gilman's The Pharmacological Basis of Therapeutics, 9th ed., eds. Hardman, et al. (McGraw Hill, 1996); and U.S. Pat. No. 5,977,159.)

Within this application, unless otherwise stated, the techniques utilized may be found in any of several well-known references such as: Molecular Cloning: A Laboratory Manual(Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, $2_{nd}$Ed. (R. I. Freshney. 1987. Liss, Inc. New York, N.Y.), Gene Transfer and Expression Protocols, pp. 109–128, ed. E. J. Murray, The Humana Press Inc., Clifton, N.J.), and the Ambion 1998 Catalog (Ambion, Austin, Tex.).

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The biological formation of angiotensin is initiated by the action of renin on the plasma substrate angiotensinogen (Circulation Research 60:786–790 (1987); Clouston et al., Genomics 2:240–248 (1988); Kageyama et al., Biochemistry 23:3603–3609; Ohkubo et al., Proc. Natl. Acad. Sci. 80:2196–2200 (1983)); all references hereby incorporated in their entirety). The substance so formed is a decapeptide called angiotensin I (AI) which is converted to AII by the converting enzyme angiotensinase which removes the C-terminal His-Leu residues from AI, Asp-Arg-Val-Tyr-Ile-His-Pro-Phe-His-Leu [SEQ ID NO:37]. AII is a known pressor agent and is commercially available.

Studies have shown that AII increases mitogenesis and chemotaxis in cultured cells that are involved in wound repair, and also increases their release of growth factors and extracellular matrices (dizerega, U.S. Pat. No. 5,015,629; Dzau et. al., J Mol. Cell. Cardiol. 21:S7 (Supp III) 1989; Berk et. al., Hypertension 13:305–14 (1989); Kawahara, et al., BBRC 150:52–9 (1988); Naftilan, et al., J. Clin. Invest. 83:1419–23 (1989); Taubman et al., J. Biol. Chem. 264:526–530 (1989); Nakahara, et al., BBRC 184:811–8 (1992); Stouffer and Owens, Circ. Res. 70:820.(1992); Wolf, et al., Am. J. Pathol. 140:95–107 (1992); Bell and Madri, Am. J. Pathol. 137:7–12 (1990)). In addition, AII was shown to be angiogenic in rabbit corneal eye and chick chorioallantoic membrane models (Fernandez, et al., J Lab. Clin. Med. 105:141 (1985); LeNoble, et al., Eur. J. Pharnacol. 195:305–6 (1991)).

The effect of AII on a given cell type has been hypothesized to be dependent, in part, upon the AII receptor subtype(s) the cell expresses (Shanugam et al., Am. J. Physiol. 268:F922–F930 (1995); Helin et al., Annals of Medicine 29:23–29 (1997); Bedecs et al., Biochem J. 325:449–454 (1997)). These studies have shown that AII receptor subtype expression is a dynamic process that changes during development, at least in some cell types. AII activity is typically modulated by either or both the AT1 and AT2 AII receptors. However, AII has recently been shown to stimulate proliferation of primary human keratinocytes via a non-AT1, non-AT2 receptor. (Steckelings et al., Biochem. Biophys. Res. Commun. 229:329–333 (1996)). These results underscore the cell-type (ie: based on receptor expression) specific nature of AII activity.

The effects of AII receptor and AII receptor antagonists have been examined in two experimental models of vascular injury and repair which suggest that both AII receptor subtypes (AT1 and AT2) play a role in wound healing (Janiak et al., *Hypertension* 20:737–45 (1992); Prescott, et al., *Am. J. Pathol.* 139:1291–1296 (1991); Kauffman, et al., *Life Sci.* 49:223–228 (1991); Viswanathan, et al., *Peptides* 13:783–786 (1992); Kimura, et al., BBRC 187:1083–1090 (1992).

Many studies have focused upon AII(1–7) (AII residues 1–7) or other fragments of AII to evaluate their activity. AII(1–7) elicits some, but not the full range of effects elicited by AII. (Pfeilschifter, et al., *Eur. J Pharmacol.* 225:57–62 (1992); Jaiswal, et al., *Hypertension* 19(Supp. II):II-49-II-55 (1992); Edwards and Stack, *J. Pharmacol. Exper. Ther.* 266:506–510 (1993); Jaiswal, et al., *J. Pharmacol. Exper. Ther.* 265:664–673 (1991); Jaiswal, et al., *Hypertension* 17:1115–1120 (1991); Portsi, et a., *Br. J. Pharmacol.* 111:652–654 (1994)).

Other data suggests that the AII fragment AII(1–7) acts through a receptor(s) that is distinct from the AT1 and AT2 receptors which modulate AII activity. (Ferrario et al., J. Am. Soc. Nephrol. 9:1716–1722 (1998); Iyer et al., Hypertension 31:699–705 (1998); Freeman et al., Hypertension 28:104 (1996); Ambuhl et al., Brain Res. Bull. 35:289 (1994)). Thus, AII(1–7) activity on a particular cell type cannot be predicted based solely on the effect of AII on the same cell type. In fact, there is some evidence that AII(1–7) often opposes the actions of AII. (See, for example, Ferrario et al., Hypertension 30:535–541 (1997))

We have previously demonstrated that angiotensinogen, angiotensin I (AI), AI analogues, AI fragments and analogues thereof, angiotensin II (AII), AII analogues, AII fragments or analogues thereof; AII AT$_2$ type 2 receptor agonists (hereinafter referred to as the "active agents") are effective in accelerating wound healing and the proliferation of certain cell types, including epithelial cells and keratinocytes. See, for example, co-pending U.S. patent application Ser. Nos. 09/012,400 (Jan. 23, 1998); 09/198,806 (Nov. 24, 1998); 09/264,563 (Filed Mar. 8, 1999); 09/287,674 (Filed Apr. 7, 1999); 09/307,940(Filed May 10, 1999); 09/246,162 (Filed Feb. 8, 1999); 09/255,136 (Filed Feb. 19, 1999); 09/245,680 (Filed Feb. 8, 1999); 09/250,703 (Filed Feb. 15, 1999); 09/246,525 (Filed Feb. 8, 1999); 09/266,293 (Filed Mar. 11, 1999); 09/332,582 (Filed Jun. 14, 1999); 09/373,962 (Filed Aug. 13, 1999); and 09/352,191 (Filed Mar. 11, 1999); as well as U.S. Pat. Nos. 5,015,629; 5,629,292; 5,716,935; 5,834,432; and 5,955,430; all references incorporated herein by reference in their entirety.

However, previous studies demonstrate that fetal wounds heal without scar formation, and a well characterized aging mouse colony exhibits a reduction in scarring after wound healing. (Ashcroft et al., J. Anat. 190:351–365 (1997)). Thus, the processes of wound healing and scar formation are separable. Furthermore, administration of antibodies to TGF-P1 and TGF-β2 to healing adult rodents with dermal wounds did not effect the wound healing response, but caused a reduction in scar formation. (Chamberlin et al., J. Anat. 186:87–96 (1995)) Thus, factors that promote wound healing do not necessarily limit scar formation.

Based on all of the above, it is not known whether angiotensinogen, AI, AI analogues, and/or AI fragments and analogues thereof, AII analogues, AII fragments or analogues thereof, ACE inhibitors, and/or AII AT$_2$ type 2 receptor agonists limit scar formation and adhesion formation.

A peptide agonist selective for the AT2 receptor (AII has 100 times higher affinity for AT2 than AT1) is p-aminophenylalanine6-AII ["(p-NH$_2$-Phe)6-AII)"], Asp-Arg-Val-Tyr-Ile-Xaa-Pro-Phe [SEQ ID NO.36] wherein Xaa is p-NH$_2$-Phe (Speth and Kim, BBRC 169:997–1006 (1990). This peptide gave binding characteristics comparable to AT2 antagonists in the experimental models tested (Catalioto, et al., *Eur. J. Pharmacol.* 256:93–97 (1994); Bryson, et al., *Eur. J. Pharmacol.* 225:119–127 (1992).

The effects of AII receptor and AII receptor antagonists have been examined in two experimental models of vascular injury and repair which suggest that both AII receptor subtypes (AT1 and AT2) play a role in wound healing (Janiak et al., *Hypertension* 20:737–45 (1992); Prescott, et al., *Am. J. Pathol.* 139:1291–1296 (1991); Kauffman, et al., *Life Sci.* 49:223–228 (1991); Viswanathan, et al., *Peptides* 13:783–786 (1992); Kimura, et al., BBRC 187:1083–1090 (1992).

Many studies have focused upon AII(1–7) (AII residues 1–7) or other fragments of AII to evaluate their activity. AII(1–7) elicits some, but not the full range of effects elicited by AII. Pfeilschifter, et al., *Eur. J. Pharmacol.* 225:57–62 (1992); Jaiswal, et al., *Hypertension* 19(Supp. II):II-49-II-55 (1992); Edwards and Stack, *J. Pharmacol. Exper. Ther.* 266:506–510 (1993); Jaiswal, et al., *J. Pharmacol. Exper. Ther.* 265:664–673 (1991); Jaiswal, et al., *Hypertension* 17:1115–1120 (1991); Portsi, et a., *Br. J. Pharmacol.* 111:652–654 (1994).

As hereinafter defined, a preferred class of AT2 agonists for use in accordance with the present invention comprises AII, AII analogues or active fragments thereof having p-NH-Phe in a position corresponding to a position 6 of AII. In addition to peptide agents, various nonpeptidic agents (e.g., peptidomimetics) having the requisite AT2 agonist activity are further contemplated for use in accordance with the present invention.

The active AII analogues, fragments of AII and analogues thereof of particular interest in accordance with the present invention comprise a sequence consisting of at least three contiguous amino acids of groups $R^1$-$R^8$ in the sequence of general formula I

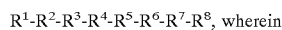
$R^1$-$R^2$-$R^3$-$R^4$-$R^5$-$R^6$-$R^7$-$R^8$, wherein $R^1$ is suitably selected from H, Asp, Glu, Asn, Acpc (1-aminocyclopentane carboxylic acid), Ala, Me$^2$Gly, Pro, Bet, Glu(NH$_2$), Gly, Asp(NH$_2$) and Suc, $R^2$ is suitably selected from Arg, Lys, Ala, Orn, Ser(Ac), Sar, D-Arg and D-Lys, $R^3$ is selected from the group consisting of Val, Ala, Leu, norLeu, Ile, Gly, Pro, Aib, Acpc and Tyr, while Lys has also been found effective at this residue;

$R^4$ is selected from the group consisting of Tyr, Tyr(PO$_3$)$_2$, Thr, Ser, homoSer, azaTyr, and Ala;

$R^5$ is selected from the group consisting of Ile, Ala, Leu, norLeu, Val and Gly;

$R^6$ is His, Arg or 6-NH$_2$-Phe;

$R^7$ is Pro or Ala; and $R^8$ is absent or is selected from the group consisting of Phe, Phe(Br), Ile and Tyr, excluding sequences including $R^4$ as a terminal Tyr group.

Particularly preferred embodiments of this class of compounds are SEQ ID NO:2, SEQ ID NO:4, SEQ ID NO:13, SEQ ID NO:18, SEQ ID NO:19, SEQ ID NO:26, SEQ ID. NO:31, SEQ ID NO:34, and SEQ ID NO:38.

Compounds falling within the category of AT2 agonists useful in the practice of the invention include the AII analogues set forth above subject to the restriction that $R^6$ is p-NH$_2$-Phe.

Particularly preferred combinations for $R^A$ and $R^B$ are Asp-Arg, Asp-Lys, Glu-Arg and Glu-Lys. Particularly preferred embodiments of this class include the following: AIII or AII(2–8), Arg-Val-Tyr-Ile-His-Pro-Phe [SEQ ID NO:2]; AII(3–8), also known as des1-AIII or AIV, Val-Tyr-Ile-His-Pro-Phe [SEQ ID NO:3]; AII(1–7), Asp-Arg-Val-Tyr-Ile-His-Pro {SEQ ID NO:4]; AII(2–7). Arg-Val-Tyr-Ile-His-Pro [SEQ ID NO:5]; AII(3–7), Val-Tyr-Ile-His-Pro [SEQ ID NO:6]; AII(5–8), Ile-His-Pro-Phe [SEQ ID NO:7]; AII(1–6), Asp-Arg-Val-Tyr-Ile-His [SEQ ID NO:8]; AII(1–5), Asp-Arg-Val-Tyr-Ile [SEQ ID NO:9]; AII(1–4), Asp-Arg-Val-Tyr [SEQ ID NO:10]; and AII(1–3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(6–8), His-Pro-Phe [SEQ ID NO:14] and AII(4–8), Tyr-Ile-His-Pro-Phe [SEQ ID NO:15] were also tested and found not to be effective.

Another class of particularly preferred compounds in accordance with the present invention consists of those with the following general structure:

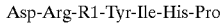

Asp-Arg-R1-Tyr-Ile-His-Pro wherein R1 is selected from the group consisting of Lys, Leu, norLeu, Val, Ile, and Ala.

Even more preferred embodiments include SEQ ID NO:4, SEQ ID:40, and SEQ ID NO:41, with SEQ ID NO:41 being the most preferred embodiment.

Another class of compounds of particular interest in accordance with the present invention are those of the general formula II

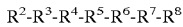

$R^2$-$R^3$-$R^4$-$R^5$-$R^6$-$R^7$-$R^8$ in which $R^2$ is selected from the group consisting of H, Arg, Lys, Ala, Orn, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr(PO$_3$)$_2$, Thr, Ser, homoSer, azaTyr, and Ala;

$R^5$ is selected from the group consisting of Ile, Ala, Leu, norLeu, Val and Gly;

$R^6$ is His, Arg or 6-NH$_2$-Phe;

$R^7$ is Pro or Ala; and $R^8$ is selected from the group consisting of Phe, Phe(Br), Ile and Tyr.

A particularly preferred subclass of the compounds of general formula II has the formula

$R^2$-$R^3$-Tyr-$R^5$-His-Pro-Phe [SEQ ID NO:16]

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4–8) was ineffective in repeated tests; this is believed to be due to the exposed tyrosine on the N-terminus.

Other particularly preferred embodiments include:

| | | | |
|---|---|---|---|
| 1GD | Ala4-AII(1–7) | DRVAIHP | SEQ ID NO:38 |
| 2GD | Pro3-AII(1–7) | DRPYIHP | SEQ ID NO:39 |
| 5GD | Lys3-AII(1–7) | DRKYIHP | SEQ ID NO:40 |
| 9GD | NorLeu-AII(1–7) | DR(nor)YIHP | SEQ ID NO:41 |
| GSD 28 | Ile$^8$-AII | DRVYIHPI | SEQ ID NO:42 |
| | Ala3aminoPhe6 AII: | DRAYIF*PF | SEQ ID NO:43 |
| | Ala3-AIII | RVAIHPF | SEQ ID NO:44 |
| | Gly$^1$-AII | GRVYIHPF | SEQ ID NO:45 |
| | NorLeu$^4$-AIII | --RVYnLHPF | SEQ ID NO:46 |
| | Acpc$^3$-AII | DR(Acpc)YIHPF | SEQ ID NO:47 |
| GSD 37B | Orn$^2$-AII | D(Orn)VYIHPF | SEQ ID NO:48 |
| GSD 38B | Citron$^2$-AII | D(Citron)VYIHPF | SEQ ID NO:49 |
| 3GD | Pro$^3$Ala$^4$-AII(1–7) | DRPAIHP | SEQ ID NO:50 |

In the above formulas, the standard three-letter abbreviations for amino acid residues are employed. In the absence of an indication to the contrary, the L-form of the amino acid is intended. Other residues are abbreviated as follows:

TABLE 1

Abbreviation for Amino Acids

| | |
|---|---|
| Me$^2$Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

It has been suggested that AII and its analogues adopt either a gamma or a beta turn (Regoli, et al., *Pharmacological Reviews* 26:69 (1974). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, norLeu, Ile, Gly, Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr $(PO_3)_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). It has also been found that $R^4$ can be Ala.

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, Gly and Val.

In the angiotensinogen, AI, AI analogues, AI fragments and analogues thereof, AII analogues, fragments and analogues of fragments of particular interest in accordance with the present invention, $R^6$ is His, Arg or 6-$NH_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and an anionic carboxyl terminal appear to be particularly useful in binding of the analogues of interest to receptors; therefore, Tyr and especially Phe are preferred for purposes of the present invention.

Analogues of particular interest include the following:

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NO: 27 |
| Analogue 10 | Asp-Arg-Val-Tyr-Ile-His-Ala-Phe | SEQ ID NO: 28 |
| Analogue 11 | Asp-Arg-Val-Tyr-Ile-His-Pro-Tyr | SEQ ID NO: 29 |
| Analogue 12 | Pro-Arg-Val-Tyr-Ile-His-Pro-Phe | SEQ ID NO: 30 |
| Analogue 13 | Asp-Arg-Pro-Tyr-Ile-His-Pro-Phe | SEQ ID NO: 31 |
| Analogue 14 | Asp-Arg-Val-Tyr($PO_3)_2$-Ile-His-Pro-Phe | SEQ ID NO: 32 |
| Analogue 15 | Asp-Arg-norLeu-Tyr-Ile-His-Pro-Phe | SEQ ID NO: 33 |

TABLE 2-continued

Angiotensin II Analogues

| AII Analogue Name | Amino Acid Sequence | Sequence Identifier |
|---|---|---|
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be synthesized by any conventional method, including, but not limited to, those set forth in J. M. Stewart and J. D. Young, *Solid Phase Peptide Synthesis*, 2nd ed., Pierce Chemical Co., Rockford, Ill. (1984) and J. Meienhofer, *Hormonal Proteins and Peptides*, Vol. 2, Academic Press, New York, (1973) for solid phase synthesis and E. Schroder and K. Lubke, *The Peptides*, Vol. 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

In one aspect, the present invention provides a method of limiting scar formation by administering to a mammal in need thereof an amount effective of angiotensinogen, AI, AI analogues, and/or AI fragments and analogues thereof, AII analogues, AII fragments and analogues thereof, ACE inhibitors, and/or AII $AT_2$ type 2 receptor agonists ("active agents"), either alone or in combination with other compounds that serve to limit scar or adhesion formation. In a preferred embodiment, the active agent is selected from the group consisting of SEQ ID NO:4, SEQ ID NO:40, and SEQ ID NO:41. In a most preferred embodiment, the active agent comprises SEQ ID NO:41. Additional compounds to limit scar formation include, but are not limited to inhibitors of TGF-β1 and TGF-β2.

In another aspect, the present invention provides a method of limiting adhesion formation by administering to a mammal in need thereof an amount effective of angiotensinogen, AI, AI analogues, and/or AI fragments and analogues thereof, AII analogues, AII fragments and analogues thereof, ACE inhibitors, and/or AII $AT_2$ type 2 receptor agonists ("active agents"), either alone or in combination with other compounds that serve to limit scar or adhesion formation. In a preferred embodiment, the active agent is selected from the group consisting of SEQ ID NO:4, SEQ ID NO:40, and SEQ ID NO:41. In a most preferred embodiment, the active agent comprises SEQ ID NO:41. Additional compounds to limit adhesion formation include, but are not limited to lazaroids (U.S. Pat. No. 5,614,515), quinacrine (U.S. Pat. No. 5,478, 837) retinoids (U.S. Pat. No. 5,534,261), dipyridamole (U.S. Pat. No. 5,498,613), manoalides (U.S. Pat. No. 5,891,460), ketotifens (U.S. Pat. No. 5,891,460), tissue plasminogen activator (TPA) (U.S. Pat. No. 4,889,722), RGD-containing peptides (Rodgers et al., Fertility and Sterility, 70:1131–1138 (1998); U.S. Pat. No. 5,629,294), recombinant hirudin (Rodgers et al., J. Invest. Surg. 9:385–391 (1996)), anti-inflammatory peptide 2 (Rodgers et al., J. Investig. Surg. 10:31–36 (1997)), non-steroidal anti-inflammatory drugs (NSAIDS) such as Tolmetin and Ibuprofen (Legrand et al., J. Invest. Surg. 8:187–194 (1995)); and anti-inflammatory corticosteroids such as Betamethasone and Dexamethasone.

For use in limiting scar or adhesion formation, the active agents may be administered by any suitable route, including orally, parentally, by inhalation, spray, rectally, transdermally, or topically in dosage unit formulations containing conventional pharmaceutically acceptable carriers, adjuvants, and vehicles. The term parenteral as used herein includes, subcutaneous, intravenous, intramuscular, intrastemal, intratendinous, intraspinal, intracranial, intrathoracic, infusion techniques or intraperitoneally.

The active agents may be made up in a solid form (including granules, powders or suppositories) or in a liquid form (e.g., solutions, suspensions, or emulsions), and may be subjected to conventional pharmaceutical operations such as sterilization and/or may contain conventional adjuvants, such as preservatives, stabilizers, wetting agents, emulsifiers, buffers etc.

While the active agents can be administered as the sole active pharmaceutical agent, they can also be used in combination with one or more other compounds. When administered as a combination, the active agents and other compounds can be formulated as separate compositions that are given at the same time or different times, or the active agents and other compounds can be given as a single composition.

For administration, the active agents are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the active agents may be dissolved in saline, water, polyethylene glycol, propylene glycol, fibrin glue, Dermabond or other cyanoacrylics, thrombogen, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The dosage regimen for limiting scar or adhesion formation with the active agents is based on a variety of factors, including the type of injury, the age, weight, sex, medical condition of the individual, the severity of the condition, the route of administration, and the particular compound employed. Dosage levels of the order of between 0.1 ng/kg and 10 mg/kg of the active agents per body weight are useful for all methods of use disclosed herein.

In a preferred embodiment of the present invention, the active agents are administered transdermally or topically. A suitable transdermal or topical dose of active ingredient of the active agents is preferably between about 0.1 ng/kg and about 10 mg/kg administered twice daily. For transdermal administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

A formulation suitable for topical administration includes liquid or semi-liquid preparations suitable for penetration through the skin (e.g., liniments, lotions, ointments, creams, or pastes) and drops suitable for administration to the eye, ear, or nose.

Transdermal means including, but not limited to, transdermal patches may be utilized to deliver the active agents to the treatment site. Transdermal formulations may be prepared by incorporating the active agent in a thixotropic or gelatinous carrier including, but not limited to, a cellulose medium, e.g., methyl cellulose or hydroxyethyl cellulose, with the resulting formulation then being packed in a transdermal device adapted to be secured in dermal contact with the skin of a wearer.

In a further aspect, the present invention provides kits for limiting scar or adhesion formation, wherein the kits comprise an effective amount of the active agents of the invention, and instructions for using the amount effective of active agent to limit scar or adhesion formation.

In a still further aspect, the present invention provides pharmaceutical compositions comprising an amount effective of the active agents to limit scar or adhesion formation. In a preferred embodiment, the active agent is selected from the group consisting of SEQ ID NO:4, SEQ ID NO:40, and SEQ ID NO:41. In a most preferred embodiment, the active agent comprises SEQ ID NO:41.

In a further aspect, the pharmaceutical compositions are combined with other compounds useful for scar or adhesion formation. Such other compounds useful for preventing scar formation include, but are not limited to inhibitors of TGF-β1 and TGF-β2. Such other compounds useful for preventing adhesion formation include, but are not limited to lazaroids, quinacrine, retinoids, dipyridamole, manoalides, ketotifens, RGD peptides, recombinant hirudin, anti-inflammatory peptide 2, tissue plasminogen activator, non-steroidal anti-inflammatory drugs (NSAIDS) such as Tolmetin and Ibuprofen, and anti-inflammatory corticosteroids such as Betamethasone and Dexamethasone.

The present invention, by providing methods and kits for limiting scar formation, will be clinically useful for treating all types of wounds, both for limiting initial scar formation, and for therapeutic treatment of existing scars (i.e.: cutting out the scar after its formation, treating it with the compounds of the invention, and letting the scar heal more slowly). Such wounds include, but are not limited to lacerations, burns, punctures, trauma, ulcers, periodontal conditions, laparotomy wounds, incisional wounds, revision of hypertrophic scars, genetic hypertrophic scars, keloid scars, contractures after burns, and cosmetic surgical procedures.

The present invention, by providing methods and kits for limiting adhesion formation, will be clinically useful for use with all types of surgical procedures in which it is desired to inhibit the adhesion formation, or to reduce the amount of previously formed adhesions. It is thus broadly useful in all types of surgery in which adhesion formation can be a complication. Non-limiting examples of instances where prophylactic and/or therapeutic treatment with the compounds of the invention are of utility include tendon, ligament, abdominal, pelvic, pericardial/epicardial, neurological (including dura matter and perineural adhesions), retrosternal adhesions, and perispinal fibrosis. The methods are thus useful for specific treatments including, but not limited to, abdominal surgery, cosmetic surgery, gynecological surgery, thoracic surgery, orthopedic surgery affecting tendons, ligaments, etc., neurological surgery affecting the dura mater, peri-spinal and peri-neural adhesions, bowel obstructions, infertile women who desire to become pregnant, laminectomies, discectomies, tendon repair, arthroscopic surgery, and those patients undergoing cardiac operations who have an expectation of the need for further such treatments.

The present invention may be better understood with reference to the accompanying examples that are intended for purposes of illustration only and should not be construed to limit the scope of the invention.

EXAMPLE 1

Anti-scarring Effect of AII(1–7) Analogues

Female Sprague Dawley rats, weighing between 175 and 225 grams each, were used in this study. The rats were quarantined at least two days prior to surgery. The rats were housed in the University of Southern California vivarium on a 12:12 hour light/dark cycle. Food and water were available ad libitum except in the immediate postoperative period.

The rats underwent a standardized procedure for laparotomy (intramuscular anesthesia with ketamine/rompum, shaving with animal clippers, betadine scrub, alcohol scrub). A 2 cm incision was then made on the midline. A double-walled gelatin capsule was placed on the right side of the abdomen through the incision. The animals were subcutaneously injected with the peptides (detailed below) (100 µg/kg/day) for 3 days prior to surgery, and then for 11 days until necropsy. The abdominal wall and skin was then sutured closed using two layers of 4-0 Ethilon suture. Following surgery, the rats received analgesic for three days and were observed twice daily for signs of morbidity and mortality.

Upon gross observation following an 11 day postoperative observation period, wound closure was complete, but no scar was apparent in animals treated with the following peptides:

| 5GD: | Lys3-AII(1–7) | DRKYIHP |
| 9GD: | NorLeu3-AII(1–7) | DR(nor)YIHP |

These results demonstrate that these peptides are effective to limit scarring during wound closure.

EXAMPLE 2

Evaluation of AII(1–7) and 9GD in a Rat Full Thickness Incision Model

This study was designed to compare the effect of a daily administration of AII(1–7) and 9GD on the healing of full thickness incision wounds in a rat model. For topical administration, the viscous vehicle was prepared from carboxymethylcellulose (CMC sodium salt, low viscosity, Sigma Chemical CO., St. Louis, Mo. (Lot number 34H0310)), consisting of 10% low viscosity CMC in 0.05 M phosphate buffer, pH 7.2, and was sterilized by autoclaving followed by mixing with sterile peptide solutions or DermaBond✔/ (provided by Ethicon, Inc.), AII(1–7) and 9GD were prepared by Bachem (Torrence, Calif.) under GMP conditions.

During the experimental period, Sprague Dawley rats (5 per group) were used in this study. The rats were housed one per cage in the University of Southern California vivarium on a 12:12 hour light/dark cycle. Food and water were available ad libitum.

On the dorsal surface of the rats, two full thickness incisions (approximately 3 cm in length) were made on a prepared surface under aseptic conditions. After injury, placebo or AII(1–7) (100 µg/wound [topical], or 100 µg/kg body weight [systemic]) or 9GD (10, 100, or 500 µg/wound [topical], or 10, 100, or 500 µg/kg body weight [systemic]) was administered. The wound was sutured closed (if the peptide was not given in an adhesive base) or was closed with the placebo (in groups that have the peptide administered with cyanoacrylate (DermaBond™)).

The treatment groups included:

Surgery only

CMC control

DermaBond™ control

Pretreat systemic AII(1–7)

Systemic AII(1–7) starting on day of surgery

Systemic AII(1–7) only one dose

AII(1–7) in CMC one dose

Powder of AII(1–7)

Powder of AII(1–7) covered with DermaBond™

Pretreat systemic 9GD 10, 100, or 500 µg/kg body weight

Systemic 9GD starting on day of surgery, 10, 100, or 500 µg/kg body weight

Systemic 9GD only one dose, 10, 100, or 500 µg/kg body weight

9GD in CMC one dose 10, 100, or 500 µg per wound

Powder of 9GD

Powder of 9GD covered with DermaBond™

The animals were monitored for breathing, urination, and movement during the postoperative interval. Postoperative analgesic included twice daily administration of bupronex for 3 days post-operation. At various times after surgery (up to days), the rats were observed for the formation of scar tissue at the site of injury. On day 21, the rats were euthanized by $CO_2$ asphyxiation and tissues were harvested for histologic preparation.

Scar formation was assessed grossly, including assessment of inflammationh, dehiscence, scabbing, healing (defined as % of incision healed), and scarring. Inflammation, dehiscence, scabbing, and scarring were assessed on a 4 point scale (0, 1, 2, or 3) for none, mild, moderate, and severe, respectively. The severity of the scar was defined by the appearance of disruption, the contour of the healing site, the raising of the healing area, and the ability to note by gross observation that the wound had been made.

Figure 3:
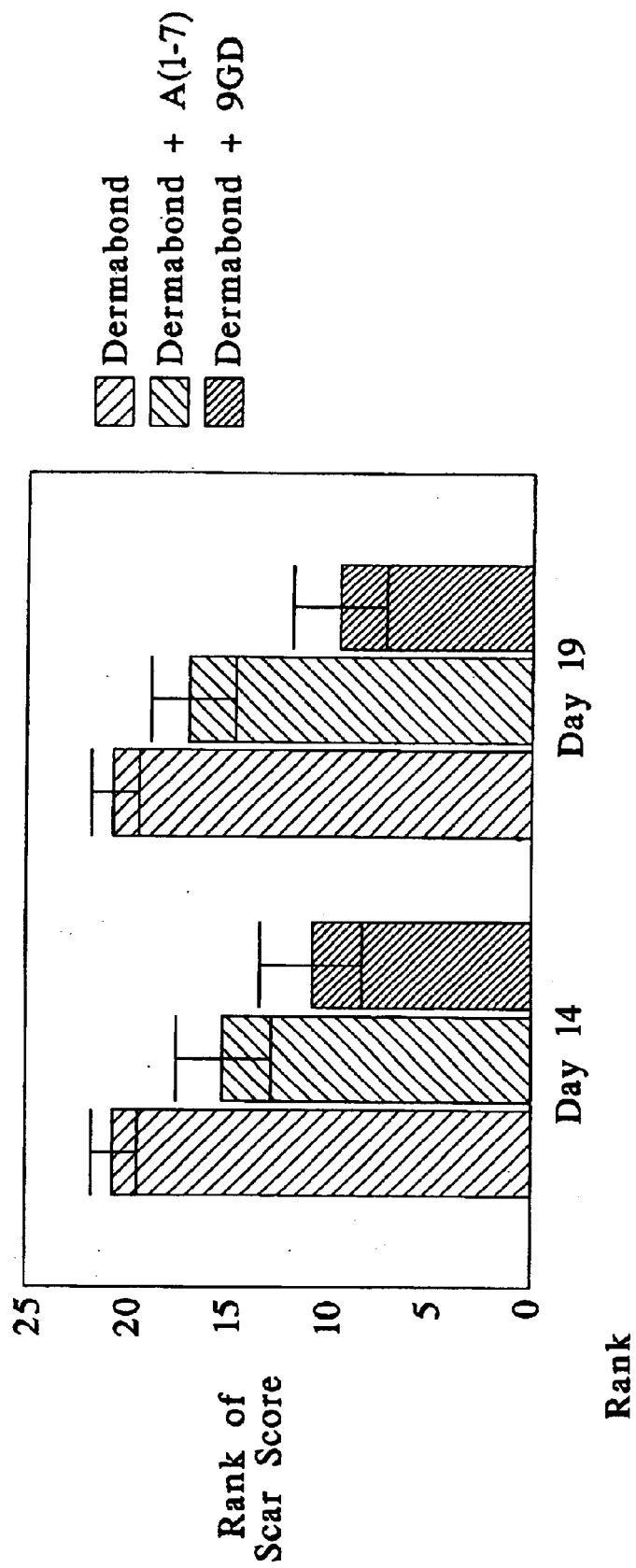
FIG. 3 is a graph showing the effect of AII(1–7) and 9GD on the scar score rank on days 14 and 19.
Figure 4:
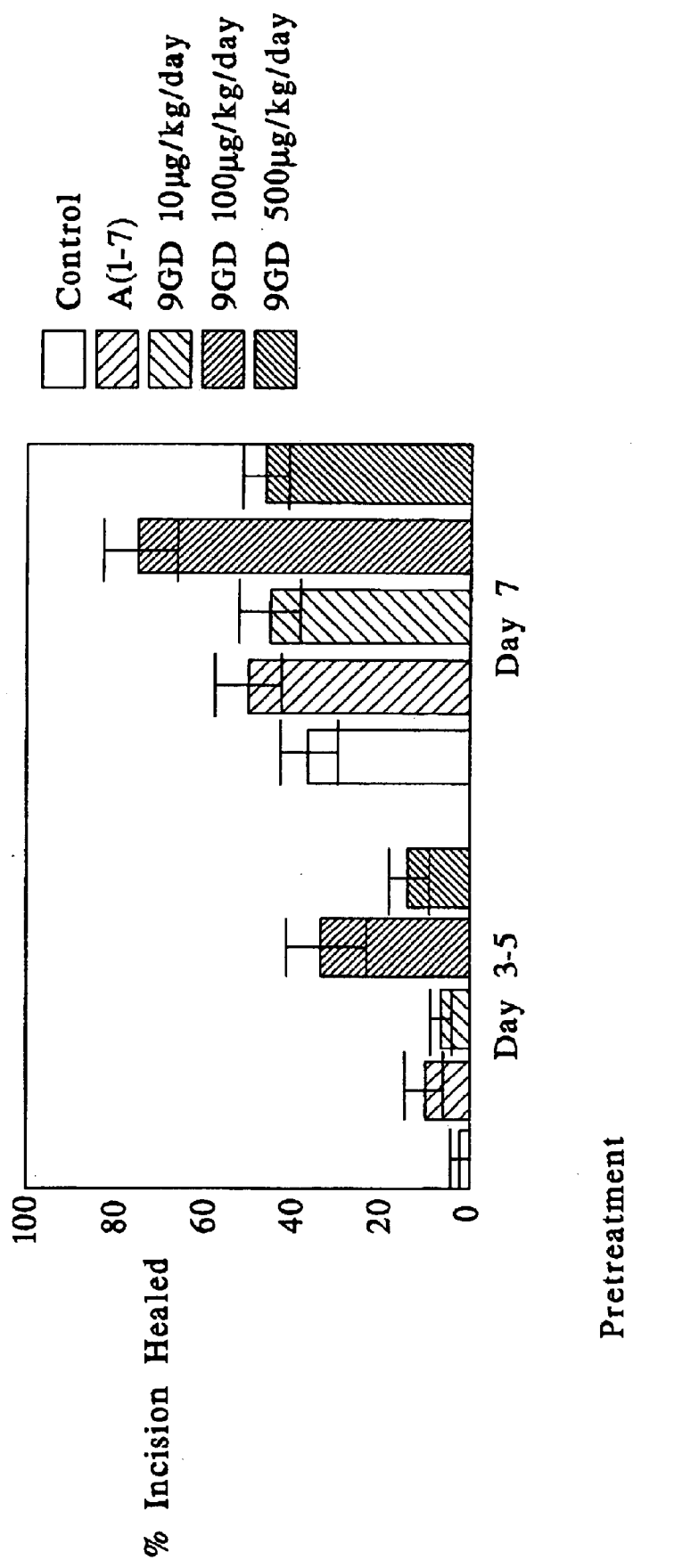
FIG. 4 is a graph showing the effect of systemically administered AII(l-7) and 9GD, given pretreatment, on incision healing on days 3–5 and 7.
Figure 5:
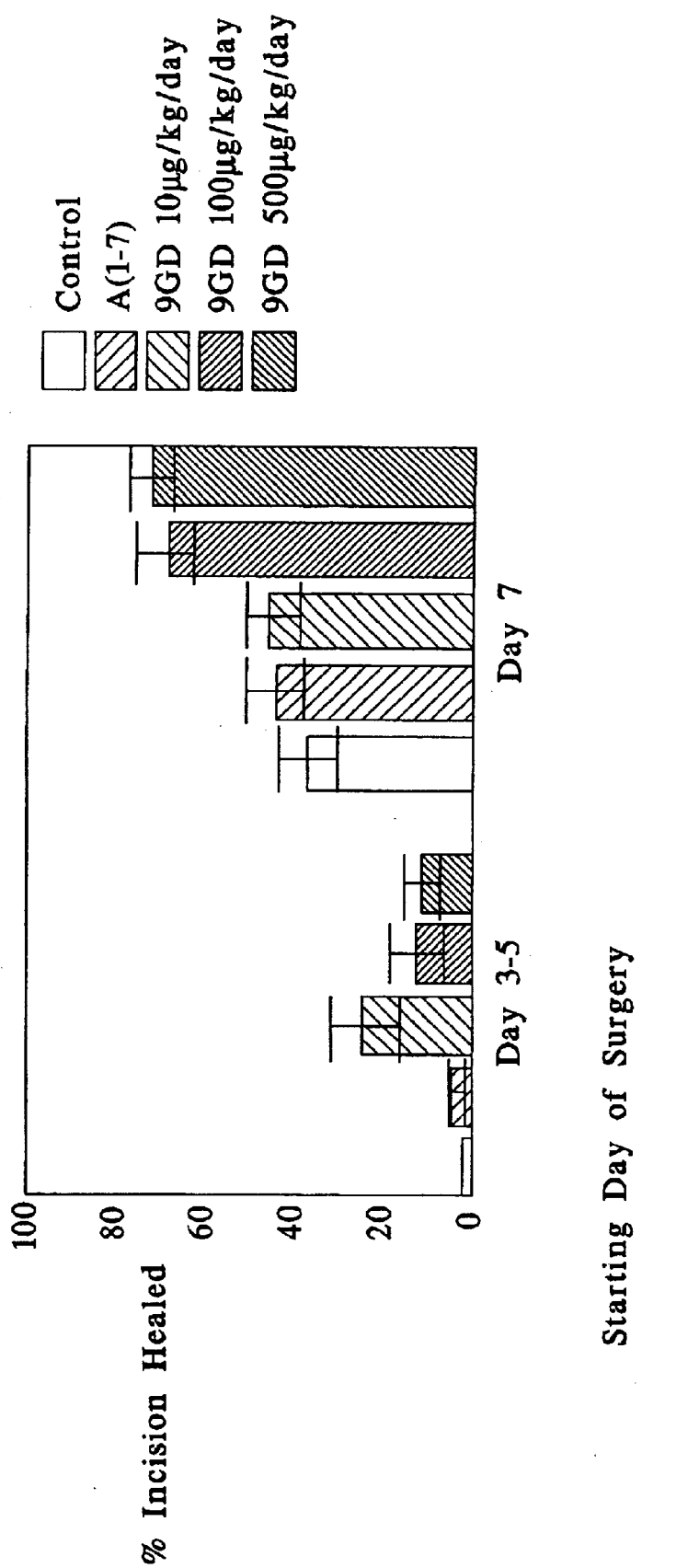
FIG. 5 is a graph showing the effect of systemically administered AII(1–7) and 9GD, starting the day of surgery, on incision healing on days 3–5 and 7.
Figure 6:
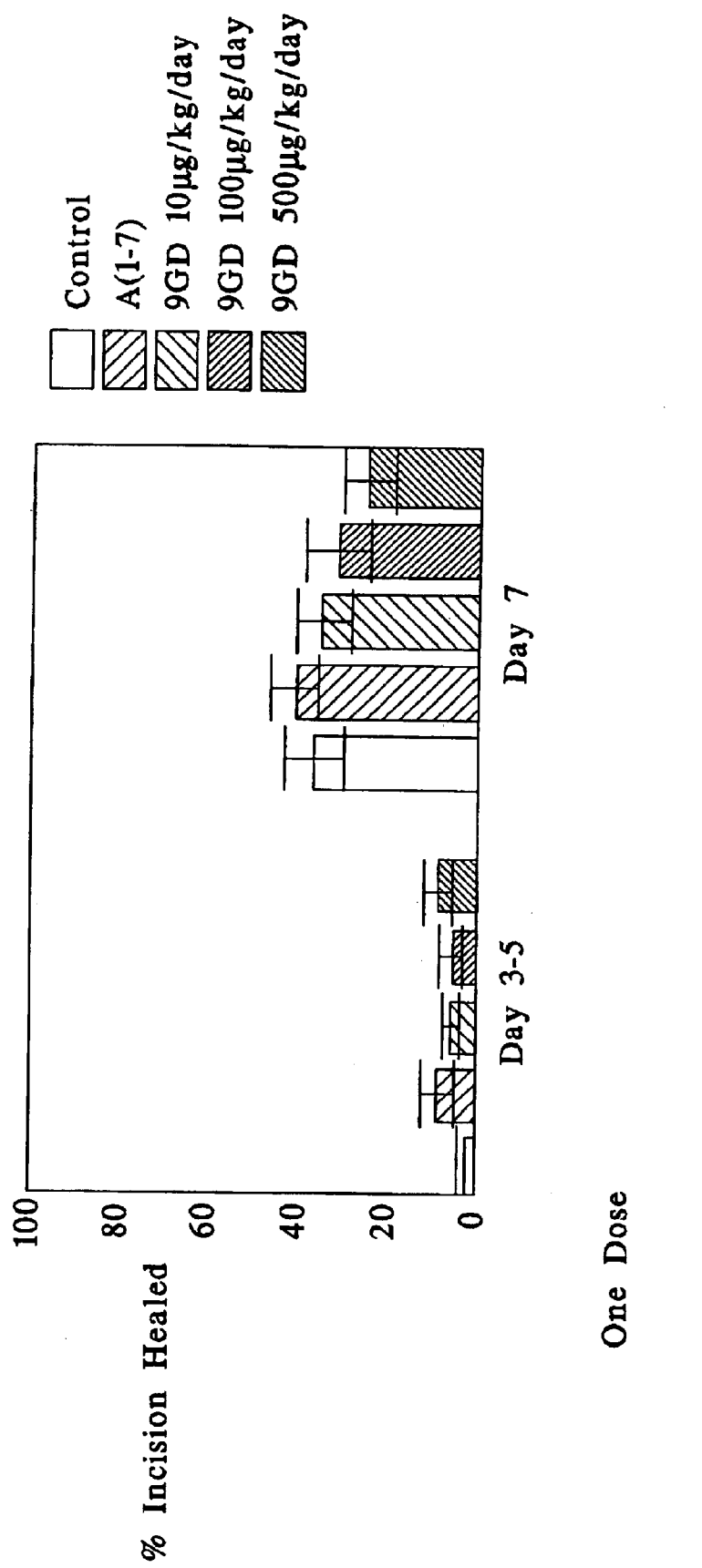
FIG. 6 is a graph showing the effect of a single dose of systemically administered AII(1 –7) and 9GD on incision healing on days 3–5 and 7
Figure 7:
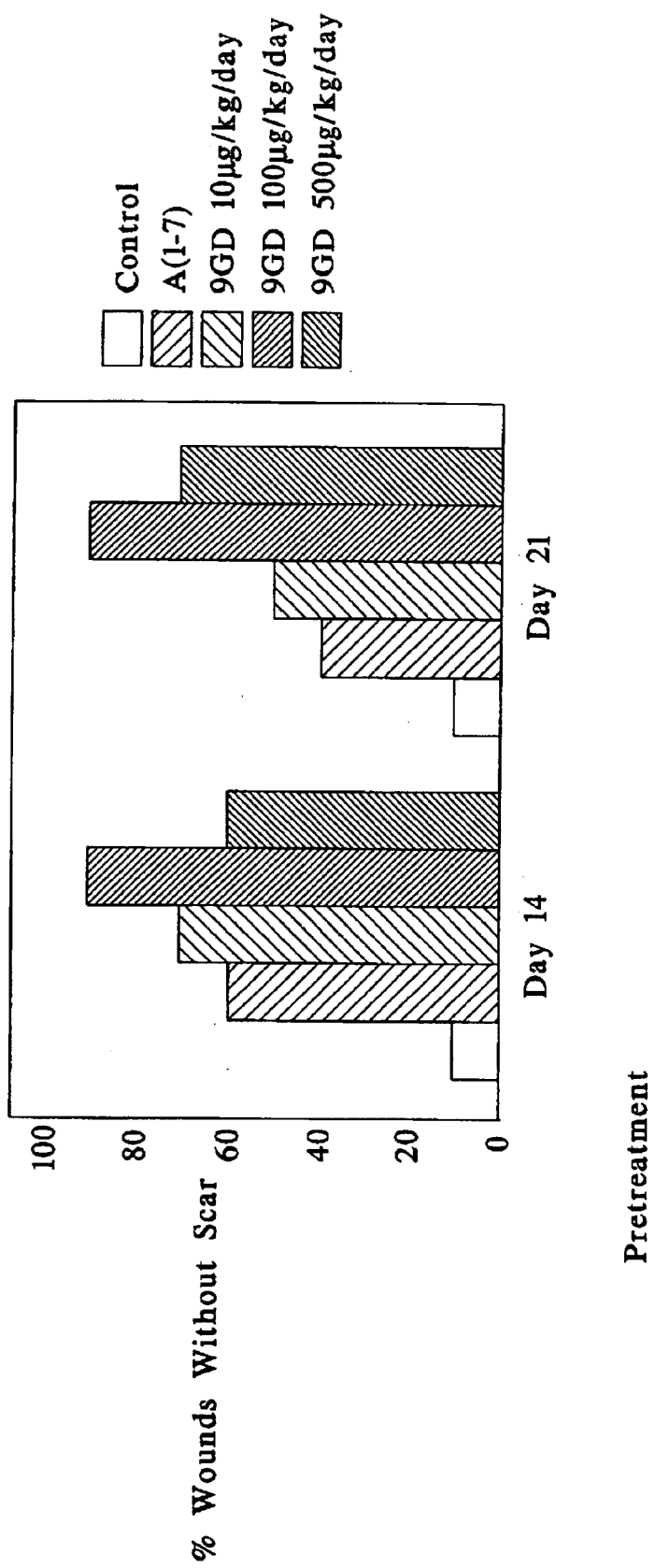
FIG. 7 is a graph showing the effect of systemically administered AII(1–7) and 9GD, given pretreatment, on the percent of wounds without scars on days 14 and 21.
Figure 8:
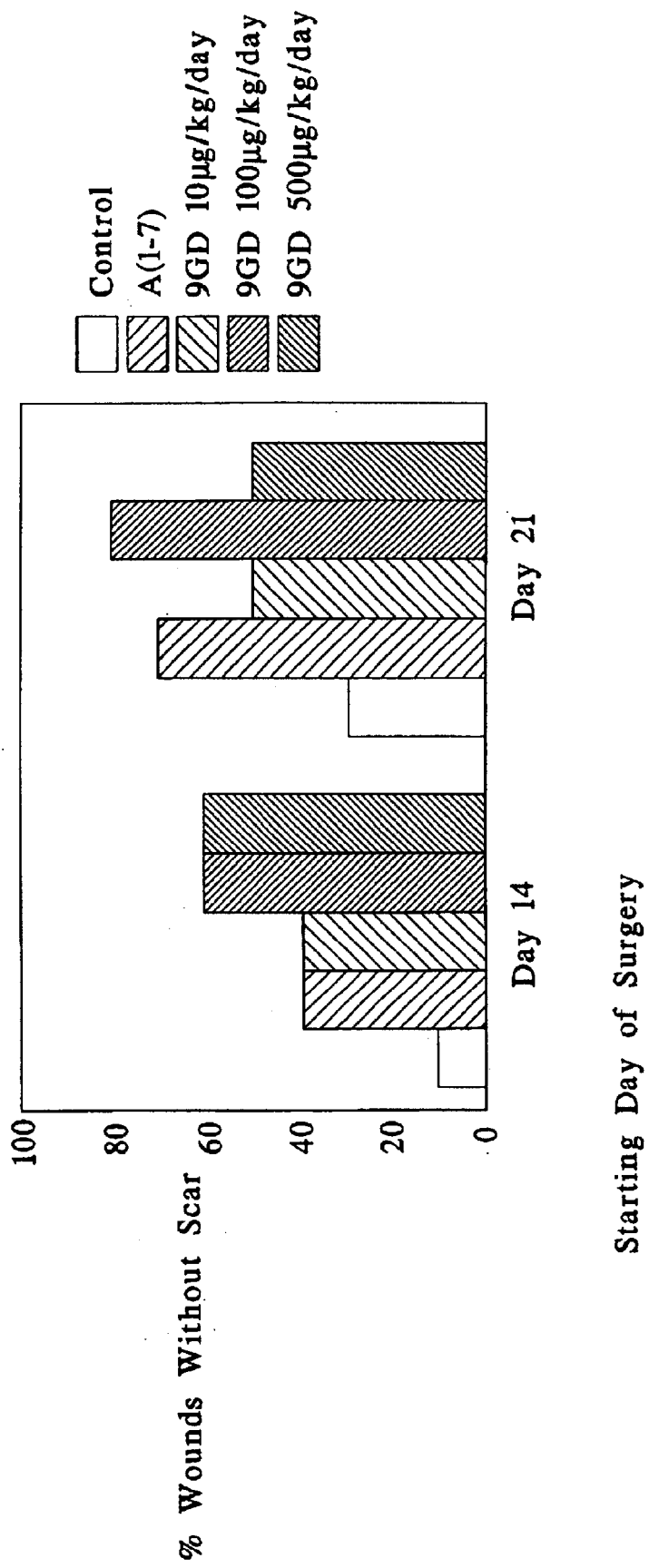
FIG. 8 is a graph showing the effect of systemically administered AII(1–7) and 9GD, given starting the day of surgery, on the percent of wounds without scars on days 14 and 21.
Figure 9:
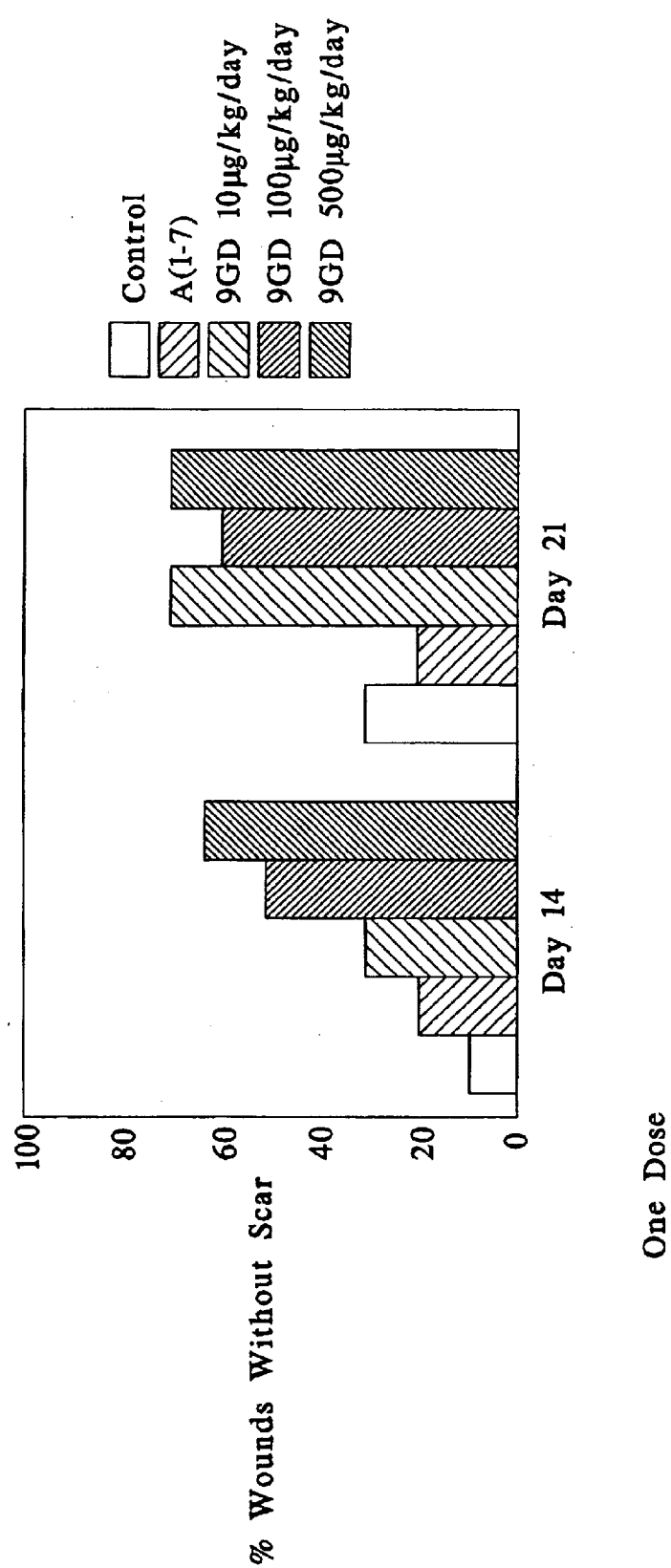
FIG. 9 is a graph showing the effect of a single dose of systemically administered AII(1–7) and 9GD on the percent of wounds without scars on days 14 and 21.
Figure 10:
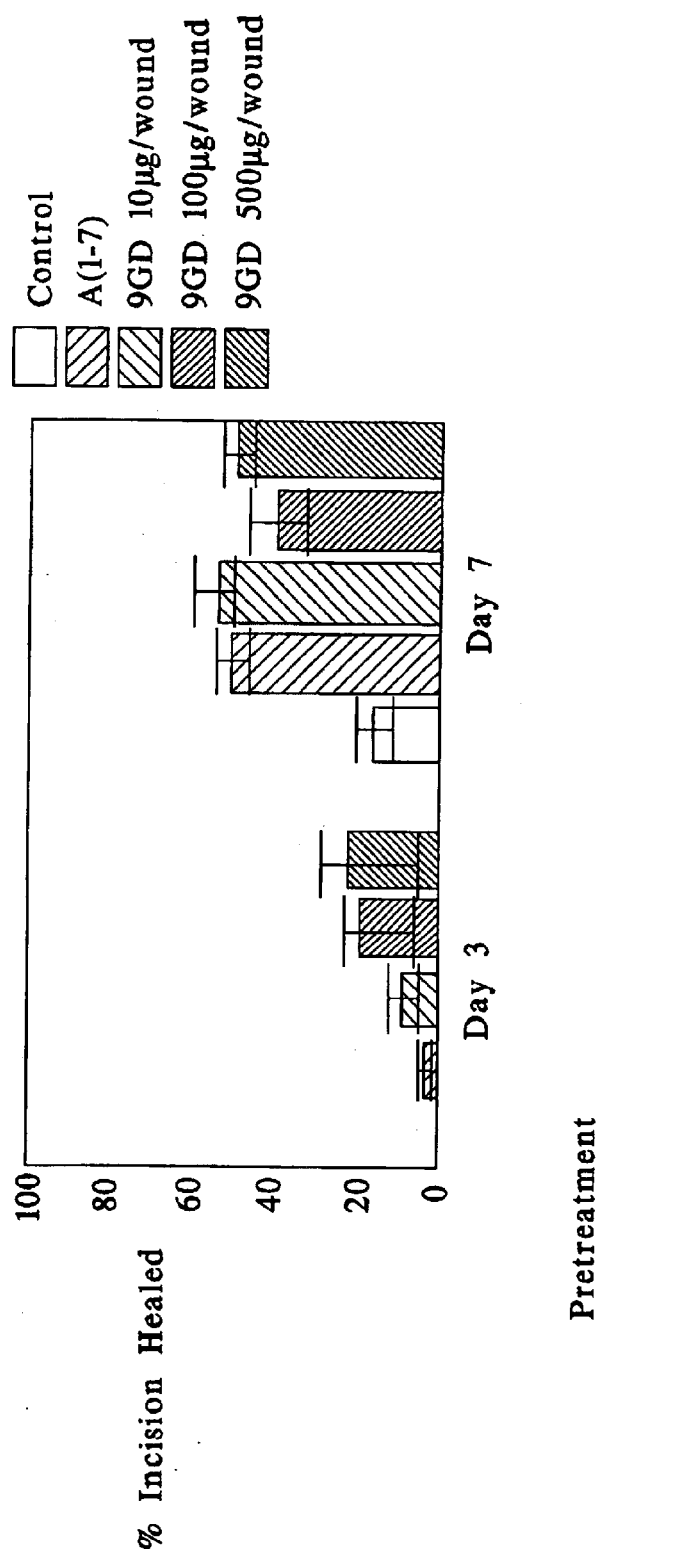
FIG. 10 is a graph showing the effect of AII(1–7) and 9GD, administered pretreatment in CMC, on the percent of incisions healed on days 3 and 7.
Figure 11:
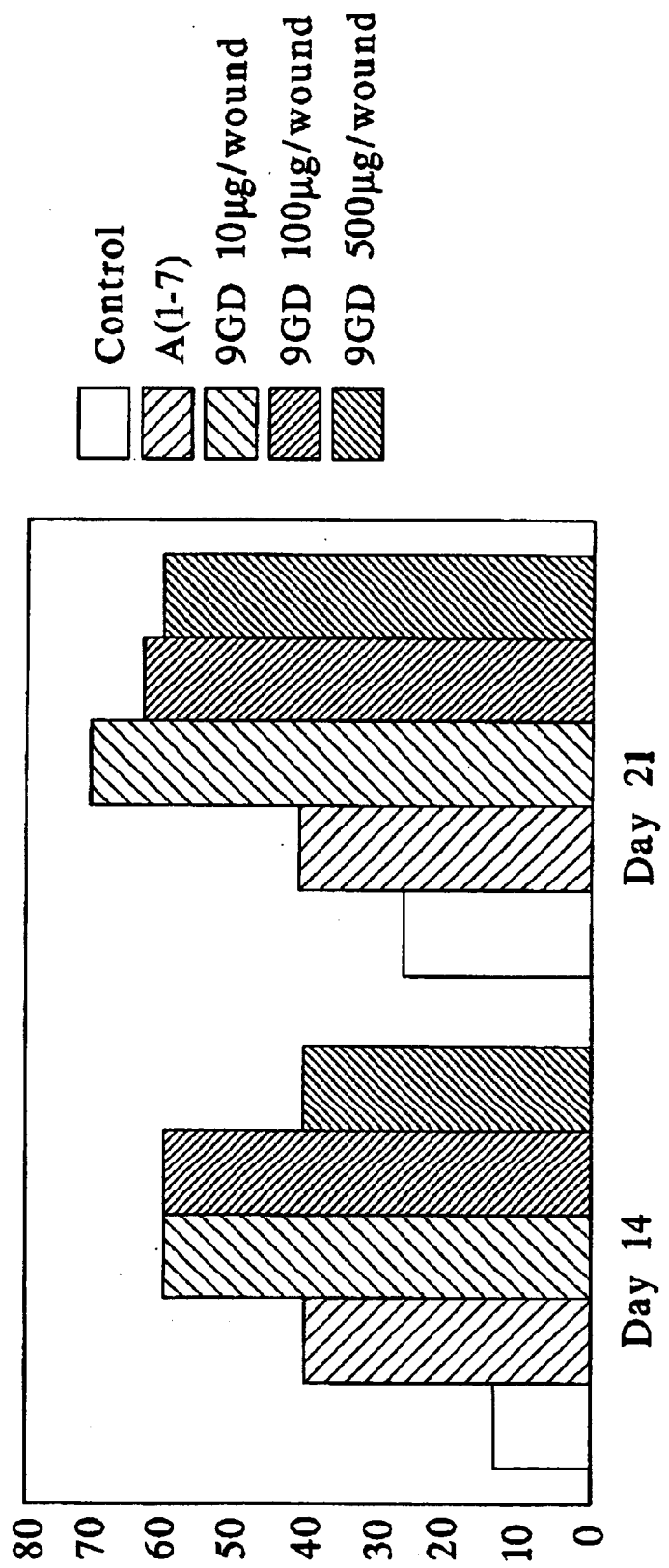
FIG. 11 is a graph showing the effect of AII(1–7) and 9GD, administered in CMC, on scar formation on days 14 and 21.

The data from these experiments is shown in FIGS. 1–11. These data show that administration of AII(1–7) and 9GD into the subcutaneous space prior to closure with DermaBond™ reduced early inflammation and wound dehiscence (FIG. 1). Further, at later time points after healing, administration of these peptides increased the number of incisions that were free of scar (FIG. 2), and overall scar formation (FIG. 3). Further, repeated, systemic administration of the peptides (especially pretreatment with 100 μg/kg body weight/day of 9GD) accelerated the healing time (to a lesser extent than they limited scar formation) (FIGS. 4–6) and increased the number of incisions with no scar by gross observations (FIGS. 7–9). A single dose of the peptides did not accelerate healing, but did reduce scar formation. A single dose of the peptides in CMC in the subcutaneous space also accelerated healing (FIG. 10) and reduced scar formation (FIG. 11).

EXAMPLE 3

Inhibition of Adhesion Formation

Multiple studies are performed to confirm the efficacy of the active agents alone or in combination with an anti-adhesion compound in the reduction of adhesion formation following peritoneal surgery. Two model systems are employed: the sidewall adhesion model and the uterine horn model. A clear correlation between results obtained using both of these models and utility in adhesion prevention has been demonstrated with INTERCEED(TC7), for which clear clinical efficacy has been shown and FDA approval for adhesion prevention in gynecological surgery has been obtained.

In the peritoneal sidewall model, rabbits are pre-anesthetized with 1.2 mg/kg acetylpromazine and anesthetized with a mixture of 55 mg/kg ketamine hydrochloride and 5 mg/kg xylazine intramuscularly. Following preparation for sterile surgery, a midline laparotomy is performed. A 3×5-cm area of peritoneum and transversus abdominis muscle is removed on the right lateral abdominal wall. The cecum is exteriorized, and digital pressure is exerted to create subserosal hemorrhages over all cecal surfaces. The cecum is then returned to its normal anatomic position. The active agent or composition thereof to be tested is placed in an Alzet miniosmotic pump (Alza Corporation, Palo Alto, Calif., USA) to allow continuous release of the molecule through the postsurgical interval. The Alzet miniosmotic pump is placed in the subcutaneous space and a delivery tube connected the pump with the site of injury at sidewall. Vehicle is placed in the pump of control rabbits. The abdominal wall and skin are closed in a standardized manner.

After 7 days, the rabbits are sacrificed and the percentage of the area of the sidewall injury that is involved in adhesions is determined. In addition, the tenacity of the adhesion formed is scored using a system as follows:

0 = No adhesions
1 = mild, easily dissectable adhesions
2 = moderate adhesions; non-dissectable, does not tear organ
3 = dense adhesions; non-dissectable, tears when removed A reduction in the area or the tenacity of the adhesions would be considered beneficial.

In additional experiments, a rabbit uterine horn model is employed. This model has been previously shown to cause severe adhesions in rabbits after surgery [Nishimura, K. et al., "The Use of Ibuprofen for the Prevention of Postoperative Adhesions in Rabbits," Am. J. Med., Vol. 77, pp. 102–106 (1984)]. The rabbits are anesthetized (130 mg/kg ketamine and 20 mg/kg acetylpromazine im) and prepared for sterile surgery. A midline laparotomy is performed and both uterine horns are surgically traumatized by abrading the serosal surface with gauze until punctate bleeding develops. Ischemia of both uterine horns is induced by removal of the collateral blood supply. In some studies, the materials are delivered to the site of injury via Alzet miniosmotic pumps and tubes as described above. In other studies, a portion of the test compositions are applied at the site of injury at the end of surgery and any remaining material is applied through the incision site prior to closing. Controls include surgical and vehicle controls. The abdominal wall and skin are closed in a standardized manner.

After 7 days, the rabbits are sacrificed and the percentage of the area of the uterine horn injury that is involved in adhesions is determined. An initial score to represent the overall extent of adhesions is given (0 to 4+). The percentage of a surface of the horn involved in adhesions to various organs is then determined.

In the model systems employed in the examples reported herein, compositions comprising the active agents of the invention will reduce the incidence of peritoneal adhesions.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

We claim:

1. A method for limiting scar or adhesion formation, comprising administering to a mammal in need thereof an amount effective to limit scar or adhesion formation of at least one active agent comprising a sequence of at least five contiguous amino acids of SEQ ID NO:41.

2. The method of claim 1 further comprising administering an amount effective to limit scar or adhesion formation of at least one other anti-scarring or anti-adhesion compound.

3. The method of claim 1, wherein the active agent comprises a sequence of at least six contiguous amino acids of SEQ ID NO:41.

4. The method of claim 1, wherein the active agent comprises the sequence of SEQ ID NO:41.

5. The method of claim 1, wherein the active agent comprises a sequence consisting of at least five contiguous amino acids of SEQ ID NO:41.

6. The method of claim 1, wherein the active agent consists of at least six contiguous amino acids of SEQ ID NO: 41.

7. The method of claim 1, wherein the active agent consists of the sequence of SEQ ID NO: 41.

8. The method of claim 1, wherein the method is for limiting scar formation.

9. The method of 8, wherein the scar is an existing scar.

10. The method of claim 1, wherein the method is for limiting adhesion formation.

11. The method of claim 1, wherein the active agent is administered topically.

12. The method of claim 1, wherein the active agent is administered transdermnally.

13. The method of claim 1, wherein the active agent is administered systemically.

14. The method of claim 1, wherein the mammal is a human.

15. The method of claim 10, wherein the mammal is a human, and wherein the human will undergo, is undergoing or has undergone a treatment selected from the group consisting of abdominal surgery, cosmetic surgery, gynecological surgery, thoracic surgery, orthopedic surgery affecting tendons or ligaments, neurological surgery affecting the dura mater, laminectomies, discectomies, arthroscopic surgery, and female infertility treatment.

16. The method of claim 15, wherein the human has peri-spinal adhesions, or peri-neural adhesions.

17. The method of claim 15 or 16 wherein the active agent is administered topically.

18. The method of claim 15 or 16 wherein the active agent is administered transdermally.

19. The method of claim 15 or 16 wherein the active agent is administered systemically.

* * * * *